United States Patent
Ku et al.

(10) Patent No.: US 7,547,953 B2
(45) Date of Patent: Jun. 16, 2009

(54) POROUS GALLIUM OXIDE FILMS AND METHODS FOR MAKING AND PATTERNING THE SAME

(75) Inventors: Anthony Yu-Chung Ku, Rexford, NY (US); Steven Alfred Tysoe, Ballston Spa, NY (US); Vinayak Tilak, Schenectady, NY (US); Peter Micah Sandvik, Clifton Park, NY (US); Sergio Paulo Martins Loureiro, Saratoga Springs, NY (US); James Anthony Ruud, Delmar, NY (US); Anis Zribi, Rexford, NY (US); Wei-Cheng Tian, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 293 days.

(21) Appl. No.: 11/699,530

(22) Filed: Jan. 29, 2007

(65) Prior Publication Data

US 2008/0180209 A1    Jul. 31, 2008

(51) Int. Cl.
*H01L 27/14* (2006.01)

(52) U.S. Cl. ............... 257/414; 257/467; 257/E31.001; 438/49; 73/31.06; 204/424; 338/34

(58) Field of Classification Search ............... 257/414, 257/E31.001
See application file for complete search history.

(56) References Cited

U.S. PATENT DOCUMENTS

| 4,045,729 A | 8/1977 | Loh ........................... 324/71 |
| 5,889,198 A | 3/1999 | Reitmeier ................. 75/25.05 |
| 6,012,327 A | 1/2000 | Seth ........................ 73/31.06 |
| 6,387,233 B1 * | 5/2002 | Guth et al. ................ 204/424 |

* cited by examiner

*Primary Examiner*—Tu-Tu V Ho
(74) *Attorney, Agent, or Firm*—Paul J. DiConza

(57) ABSTRACT

Gallium oxide films for sensing gas comprise $Ga_2O_3$ and have a porosity of at least about 30%. Such films can be formed by coating a substrate with a solution comprising: a gallium salt and a porogen comprising an organic compound comprising a hydrophilic chain and a hydrophobic chain; and heating the substrate to a temperature in the range from about 400° C. to about 600° C. while exposing the substrate to an oxygen-containing source to convert the gallium salt to a gallium oxide.

22 Claims, 2 Drawing Sheets

POROUS GALLIUM OXIDE FILMS AND METHODS FOR MAKING AND PATTERNING THE SAME

BACKGROUND OF THE INVENTION

The present disclosure is generally related to gas detecting materials and, more particularly, to porous gallium oxide films for detecting gas.

Gas sensing devices are commonly used to detect when a specific gas is present. The detection of a gas can be necessary for a variety of reasons. For example, toxic and combustible gases can be detected as a safety measure. Gas sensing devices also can be used to detect pollutants, e.g., nitrous oxides, in various applications, such as boilers, Selective Catalytic Reduction systems, turbines, and diesel engines. Such gas sensing devices often employ semiconductive materials that are affected by the gas being detected. In particular, the detection of a specific gas can be indicated by an increase in an electrical current that that flows through the semiconductive material. This current can be induced by an electromagnetic field.

Gallium oxide is currently employed as an effective semiconductive material in gas sensing devices. The type of gallium oxide currently used in gas sensing devices is nonporous, which can be easily deposited using, for example, chemical vapor deposition. However, the sensitivity of gas sensing devices utilizing nonporous gallium oxide to particular gases such as oxygen is less than desirable. It is believed that this drawback of nonporous gallium oxide is due to its limited surface area with which the surrounding gas molecules can interact.

Accordingly, it is desirable to develop a method of making gallium oxide with a higher surface area for the purpose of improving its sensitivity to certain gases.

BRIEF DESCRIPTION OF THE INVENTION

Disclosed herein are porous gallium oxide films and methods of making the same. In one embodiment, a film for sensing gas comprises $Ga_2O_3$ and has a porosity of at least about 30%.

The porous gallium oxide film can be formed using a unique method. In an embodiment, this method comprises: coating a substrate with a solution comprising a gallium salt and a porogen comprising an organic compound comprising a hydrophilic chain and a hydrophobic chain; and heating the substrate to a temperature in the range from about 400° C. to about 600° C. while exposing the substrate to an oxygen-containing source to convert the gallium salt to a gallium oxide.

The porous gallium oxide film can be patterned to form a semiconductive structure in a gas sensing device. In an embodiment, a method for patterning a gallium oxide film comprises: providing a substrate upon which a gallium oxide film having a porosity of at least about 30% resides; coating the substrate with a photoresist layer; exposing regions of the photoresist layer to actinic light; and contacting the substrate with a photoresist developer comprising a hydroxyl compound to etch away select regions of the photoresist layer and underlying regions of the gallium oxide.

This summary and other features are exemplified by the following figures and detailed description.

BRIEF DESCRIPTION OF THE DRAWING

Refer now to the figures, which are exemplary embodiments, and wherein the like elements are numbered alike.

DETAILED DESCRIPTION OF THE INVENTION

The present disclosure is directed to porous gallium oxide films for use in gas sensing devices. In particular, the gallium oxide films have a porosity of at least about 30%, for example, at least about 50%, wherein "porosity" is defined as the amount of pore space present in the total volume of a material. The gallium oxide films can be mesoporous, wherein "mesoporous" is defined as having a pore size in the range from about 2 nanometers (nm) to about 50 nm, for example, from about 2 nm to about 10 nm. Such films have a relatively high surface area due to the presence of pores therein that enable the efficient diffusion of gases into the films. As such, the sensitivity and response time of a gas sensing device containing the porous gallium oxide film is greatly improved as compared to that containing a nonporous gallium oxide film. As used herein, "sensitivity" is defined as the quotient of the electrical resistance of the sensing device in air and the electrical resistance of the sensing device in the gas to be detected. The porous gallium oxide films also retain the same electrical properties of nonporous gallium oxide films, making them particularly good gas sensing materials.

Figure 1:
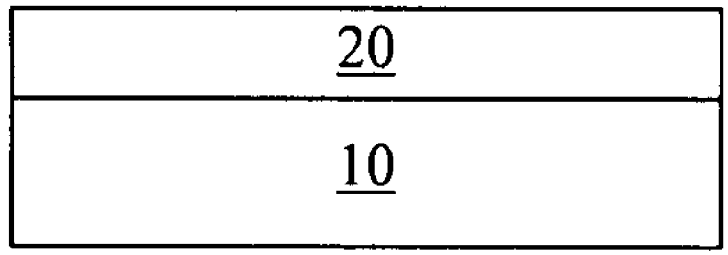
FIG. 1 is a cross-sectional view of a multi-layered topography comprising a porous gallium oxide film formed upon a substrate for use in detecting one or more particular gases.

Referring now to FIG. 1, an embodiment of a multi-layered topography for use in gas sensing devices is shown. The semiconductor topography comprises a substrate 10 upon which a mesoporous gallium oxide film 20 is formed. In one embodiment, substrate 10 is a semiconductor substrate. The term "semiconductor" refers to a substance having an electrical conductivity greater than that of an insulator and less than that of a metal, wherein its conductivity increases with temperature and in the presence of impurities, and wherein it changes from a nonconductive state to a conductive state or vice versa when charged with electricity or light. The semiconductor substrate 10 can comprise GaAs, InAs, Ge, GaN, SiC, $ZnO_2$, diamond, or a combination comprising at least one of the foregoing compounds. In an alternative embodiment, substrate 10 is an insulator substrate that has a substantially higher electrical resistance than gallium oxide film 20. The insulator substrate 10 can be arranged upon a semiconductor or conductor layer (not shown). Examples of suitable insulator materials for use in substrate 10 include but are not limited to $Al_2O_3$, mullite, $SiO_2$, MgO, or a combination comprising at least one of the foregoing compounds.

In an embodiment, mesoporous gallium oxide film 20 can be formed by first coating (e.g., spin coating) substrate 10 with a solution comprising a gallium salt and a porogen comprising an organic compound comprising a hydrophilic chain and a hydrophobic chain. As used herein, "porogen" is defined as a material that is capable of forming pores. The substrate 10 can then be heated to a temperature in the range from about 400° C. to about 1,000° C., for example, from about 400° C. to about 600° C., in the presence of an oxygen-containing source such as air. As a result of this heating step, the gallium salt can be converted to mesoporous gallium oxide having a porosity of at least about 30%, for example, at least about 50%. The minimum temperature of the heating step is selected to ensure that the resulting gallium oxide film 20 is crystalline in form and thus comprises $Ga_2O_3$. The maximum temperature is selected to ensure that gallium oxide film 20 does not undergo sintering, which could cause its porosity to be lost.

A solvent suitable for appreciably dissolving the gallium salt and the porogen, which is volatile at the temperature used to convert the gallium salt to gallium oxide, can be used in the coating solution. Examples of suitable solvents include but are not limited to alcohols such as ethanol, isopropyl alcohol, and a combination comprising at least one of the foregoing alcohols. Examples of suitable gallium salts for use in the coating solution include but are not limited to gallium nitrate hydrate, gallium chloride, gallium acetate, gallium sulfate, gallium citrate, and a combination comprising at least one of the foregoing salts.

The amount of gallium salt used can be sufficient to form gallium oxide film 20 to a thickness of in the range from about 20 nm to about 10 micrometers, for example, from about 40 nm to about 150 nm. For example, the amount of the gallium salt present in the coating solution can be in the range from about 10% to about 50%, for example, from about 10% to about 30%, by weight of the solution.

The use of an organic porogen compound comprising a hydrophilic chain and a hydrophobic chain provides for the formation of relatively large pores in gallium oxide film 20. The porogen can be, for example, a surfactant comprising a triblock copolymer of ethylene oxide and propylene oxide, $C_{16}H_{33}(OCH_2CH_2)_nOH$ ("compound 1"), where n is in the range from about 8 to about 12 (e.g., about 10), cetyltrimethylammonium chloride (CTAC), or a combination comprising at least one of the foregoing compounds. Examples of such triblock copolymers can be represented by the following formulas:

$EO_{20}PO_{70}EO_{20}$, which is commercially available from BASF Corporation under the tradename of PLURONIC P123, where "EO" is ethylene oxide and "PO" is propylene oxide $EO_{106}PO_{70}EO_{106}$, which is commercially available from BASF Corporation under the tradename of PLURONIC P123, where "EO" is ethylene oxide and "PO" is propylene oxide Compound 1 is commercially available from Sigma-Aldrich, Inc. under the tradename BRIJ 56. The amount of the porogen present in the coating solution can be in the range from about 3% to about 30%, for example, from about 5% to about 10% by weight of the solution.

A gas sensing device comprising a gallium oxide film may be employed to detect particular gases when operated at a temperature above about 300° C., such as oxygen ($O_2$), oxidizing agents, e.g., nitrous oxides (NOx), hydrogen ($H_2$), carbon monoxide (CO), ammonia ($NH_3$), or a combination comprising at least one of the foregoing compounds. For example, when the only gas sensing material present in a gas sensing device is mesoporous gallium oxide film, the device exhibits a relatively high selectivity for oxygen and oxidizing agents such as nitrous oxides. A description of suitable gas sensing devices and how they operate can be found in U.S. Pat. No. 7,053,425.

Figure 2:
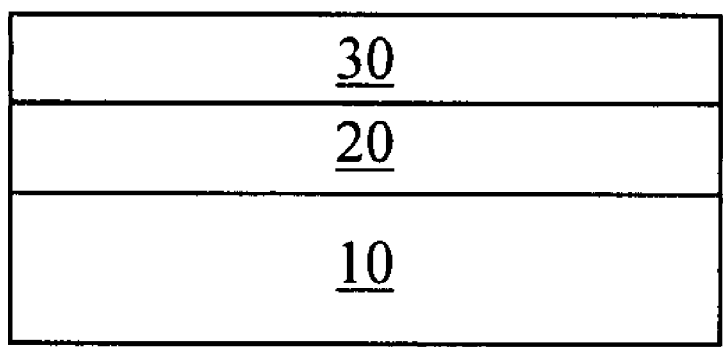
FIG. 2 is a cross-sectional view of the multi-layered topography in FIG. 1 upon which an activating material has been deposited.

On the other hand, as depicted in FIG. 2, gallium oxide film 20 can be used in conjunction an activating material 30, wherein "activating material" is defined as a material that alters the electrical properties of the gas sensing material. The activating material can alter which type of gas is being detected. While activating material 30 is shown as being arranged adjacent to gallium oxide film 20, activating material 30 can also be dispersed within pores of the gallium oxide film 20 such that it injects electrons or holes into the gallium oxide crystal lattice upon exposure to the species to be detected. In one embodiment, gas sensing material 30 can be a hydrogen sensing material for increasing the selectivity of the gas sensing device to hydrogen. Examples of suitable hydrogen sensing materials include but are not limited to titanium oxide, platinum, palladium, silver oxide, oxides of indium, vanadium, zinc, aluminum, magnesium, and a combination comprising at least one of the foregoing compounds. The hydrogen sensing material 30 can be deposited across gallium oxide film 20 using, e.g., chemical vapor deposition.

In an alternative embodiment, activating material 30 can be gallium nitride, which improves the selectivity of the gas sensing device to oxygen and oxidants. Gallium nitride is highly compatible with gallium oxide since it naturally develops a gallium oxide layer when exposed to oxygen. The gallium nitride can be disposed in the porous gallium oxide film by converting a portion of the gallium oxide into gallium nitride. This conversion can be accomplished by, for example, heating the gallium oxide film to about 900° C. in the presence of flowing ammonia for about 2 hours. A slight strain is expected in the resulting $GaN/Ga_2O_3$ structure due to the density difference between GaN (6.1 grams/cubic centimeter) and $Ga_2O_3$ (6.4 grams/cubic centimeter). The amount of conversion can be tuned by the temperature and duration of exposure to ammonia.

Figure 3:
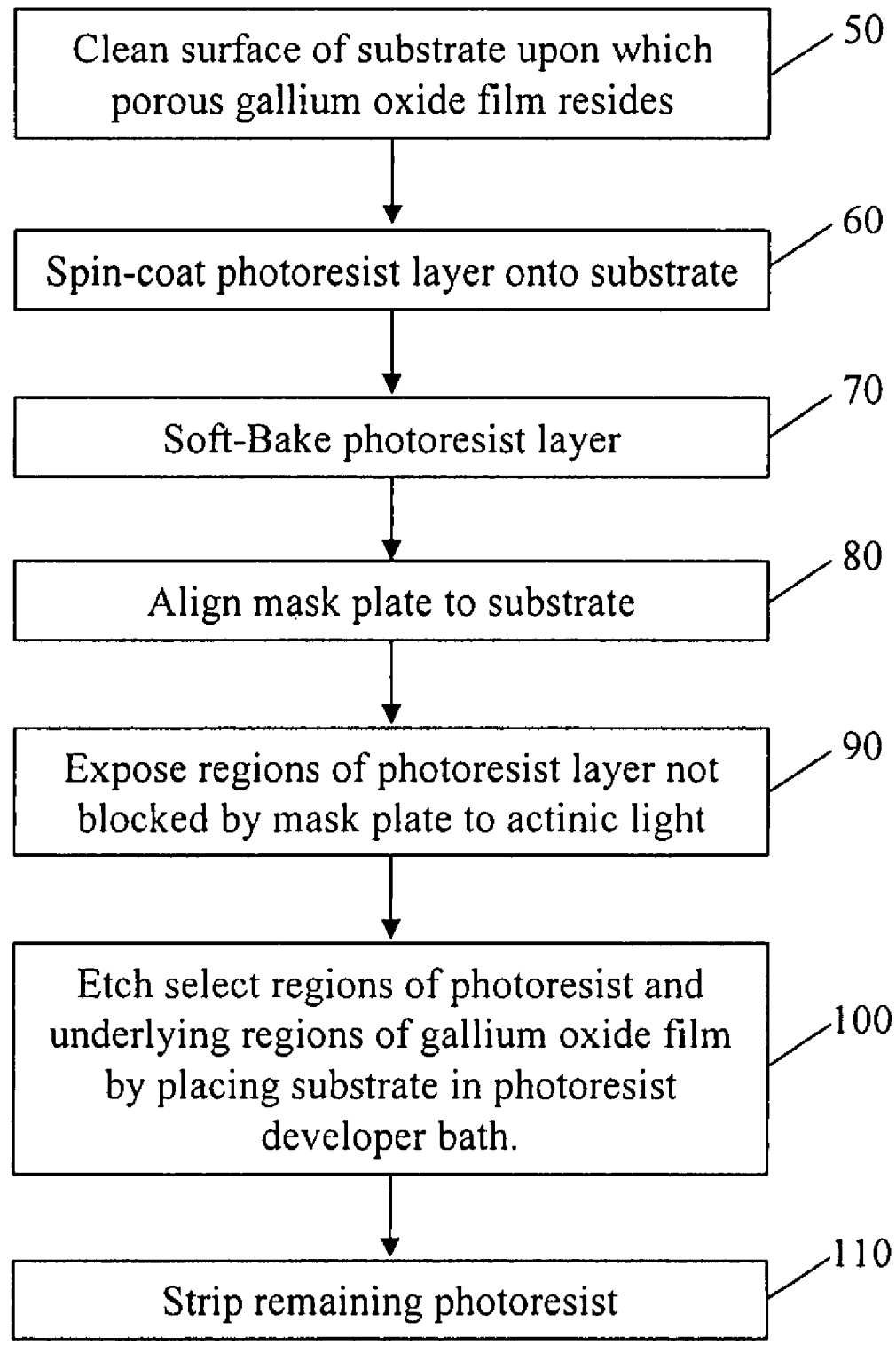
FIG. 3 is a diagram illustrating the process by which a porous gallium oxide film can be patterned during the formation of a gas sensing device.

Turning to FIG. 3, a diagram illustrating a process for patterning porous gallium oxide films is shown. The patterning of such films can be performed to make them operable as semiconductive elements in gas sensing devices. As indicated by step 50 of the process, the surface of a wafer comprising a porous gallium oxide film can be cleaned to prepare it for patterning. The porous gallium oxide film can be disposed on a silicon-based substrate. Step 50 can be performed by, for example, rinsing the surface with acetone and/or isopropyl alcohol. As indicated by step 60, the surface of the gallium oxide film can then be coated with a photoresist layer using, e.g., a standard spin-coating procedure. For example, AZ 4400 resist, commercially available from Clarion Corp., can be dispensed onto the wafer while spinning it at about 300 rotations per minute (rpm), followed by spinning the wafer at about 3,000 rpm to coat the wafer with the resist. Subsequently, as indicated by step 70, the photoresist layer can be soft-baked using the temperature and time period for the particular photoresist being used. For example, AZ 4400 resist can be soft baked at a temperature in the range from about 90° C. to about 110° C., preferably from about 100° C. to about 110° C., for a time period in the range from about 0.5 minute to about 10 minutes, preferably from about 1 minute to about 2 minutes.

Next, as indicated by step 80, a mask plate with a desired pattern can be placed adjacent to the photoresist layer and aligned to the underlying porous gallium oxide film. The mask plate can then be exposed to actinic light radiation as indicated by step 90, allowing the light to pass through transparent regions of the mask plate to the photoresist layer. Other regions of the mask plate block the light, thereby preventing it from reaching underlying regions of the photoresist layer. Alternatively, the use of a laser beam via a direct write process can be employed to eliminate the process of applying the mask plate. By exposing the photoresist layer to light, the alkali solubility of the exposed regions becomes differentiated from the non-exposed regions. In the case of a positive tone photoresist, the exposed regions become more soluble in a photoresist developing solution ("developer"), whereas in the case of a negative tone photoresist, the exposed regions become less soluble in a developer. Generally, actinic light radiation that has a wavelength sensitive to the particular photoresist can be used. Examples of actinic light radiation include but are not limited to ultraviolet light, far ultraviolet light, infrared light, an electron beam, X-rays, and the like. For example, 248 nm (KrF line), 308 nm, 365 nm (I-line), 405 nm (H-line), 436 nm (G-line), and 488 nm radiation can be used.

After the exposure step, as indicated by step 100, the photoresist layer can be contacted with a photoresist developer comprising a hydroxyl compound (e.g., potassium hydroxide (KOH), ammonium hydroxide ($NH_4OH$), or a combination comprising one of the foregoing compounds) to remove the exposed or unexposed regions thereof, depending on the type of photoresist being used. Examples of suitable hydroxyl-based developers include but are not limited to KTI-809 resist developers sold by KTI Chemical Corp., I-line resist developers sold by Shipley Company, L.L.C., and 300 MIF resist developer (tetra methyl ammonium hydroxide) sold by Clarion Corp. Removing those regions of the photoresist layer leaves underlying regions of the gallium oxide film unprotected. Surprisingly, it was discovered that those unprotected regions of the gallium oxide film can be etched with the same photoresist developer used to remove regions of the photoresist layer. Thus, the wafer containing the gallium oxide film can be placed in a wet etch bath comprising the photoresist developer to remove regions of the photoresist and underlying regions of the gallium oxide film in one step. The amount of the photoresist developer used for the wet etch bath can be, for example, more than about 50 milliLiters (mL). The photoresist developer can be mixed with deionized water, wherein the volumetric ratio of the developer to the water can be, e.g., about 2:1. This etch step can be performed at a temperature in the range from about 5° C. to about 100° C., preferably from about 18° C. to about 24° C., and more preferably at about 27° C. The length of time of the etch step can vary depending on the thickness of the gallium oxide film and the etch rate, which can be, e.g., about 7 Angstroms/second. After removing the wafer from the etch bath, the surface of the wafer can be cleaned by rinsing it with deionized water. The remaining portions of the photoresist layer can then be removed using a photoresist strip, as indicated by step 110, leaving behind a patterned gallium oxide structure such as one or more lines.

The etch process described above can result in an undercut being formed in the final gallium oxide structure such that the base of the structure is narrower than its top. This undercut could be useful for making devices such as a transistor or a Schottky diode. In particular, a second layer such as a metal layer could be deposited upon the undercut structure using, e.g., physical vapor deposition, providing for a relatively area of metal contact to the substrate.

The ability to etch both the photoresist and the gallium oxide in one step provides several advantages. For example, the etch process is compatible with current semiconductor fabrication processes and can be performed without the addition of new equipment to clean rooms where such fabrication takes place. Further, the time and therefore the cost of producing gas sensing devices comprising patterned gallium oxide are reduced by using the one step etch. As a result, large scale production of such devices can be achieved.

EXAMPLES

The following non-limiting examples further illustrate the various embodiments described herein.

Various samples of gallium oxide films were prepared by spin-coating ethanol solutions comprising gallium nitrate hydrate onto a silicon-based substrate at a spin rate of 5,000 rpm. Some of the ethanol solutions also contained a porogen. The concentrations (in weight (wt.) percent) of the components in each ethanol solution are shown in Table 1 below. Each sample was heated at 400° C. or 600° C. The thickness and porosity of each sample was then measured using variable angle spectroscopic ellipsometry modeling. As shown in Table 1, the porosity of the gallium oxide films formed using a porogen was higher than when no porogen was used. The goodness of fit parameter (MSE) from the ellipsometry modeling for each sample was also determined. The MSE values were very good for all of the samples, as indicated by being less than 20.

TABLE 1

| $[Ga(NO_3)_3]$ [wt. %] | Porogen | [Porogen] [wt. %] | Temp. [° C.] | Thickness [nm] | Porosity [%] | MSE |
|---|---|---|---|---|---|---|
| 24 | None | 0 | 400 | 59 | 20 | 17.4 |
| 10 | None | 0 | 400 | 69 | 26 | 15.0 |
| 10 | None | 0 | 600 | 64 | 26 | 6.1 |
| 10 | BRIJ 56 | 10 | 600 | 120 | 49 | 11.0 |
| 24 | BRIJ 56 | 3.3 | 400 | 123 | 54 | 6.5 |
| 24 | BRIJ 56 | 3.3 | 600 | 104 | 48 | 4.8 |
| 24 | BRIJ 56 | 10 | 400 | 129 | 49 | 7.9 |
| 24 | BRIJ 56 | 10 | 600 | 100 | 42 | 7.4 |
| 24 | CTAC | 10 | 400 | 111 | 53 | 7.2 |
| 24 | CTAC | 10 | 600 | 100 | 51 | 5.9 |
| 24 | P123 | 10 | 400 | 129 | 49 | 7.9 |
| 24 | P123 | 10 | 600 | 113 | 49 | 9.3 |

As used herein, the terms "a" and "an" do not denote a limitation of quantity, but rather denote the presence of at least one of the referenced item. Moreover, the endpoints of all ranges directed to the same component or property are inclusive of the endpoints and are independently combinable (e.g., "in the range from about 5 wt. % to about 20 wt. %," is inclusive of the endpoints 5 and 20 and all values between 5 and 20). Reference throughout the specification to "one embodiment", "another embodiment", "an embodiment", and so forth means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments. Unless defined otherwise, technical and scientific terms used herein have the same meaning as is commonly understood by one of skill in the art to which this invention belongs.

While the invention has been described with reference to an exemplary embodiment, it will be understood by those skilled in the art that various changes can be made and equivalents can be substituted for elements thereof without departing from the scope of the invention. In addition, many modifications can be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A method for forming a porous film, the method comprising:
   coating a substrate with a solution comprising a gallium salt and a porogen comprising an organic compound comprising a hydrophilic chain and a hydrophobic chain; and
   heating the substrate to a temperature in the range from about 400° C. to about 1,000° C. while exposing the substrate to an oxygen-containing source to convert the gallium salt to a gallium oxide.

2. The method of claim 1, wherein the temperature is in the range from about 400° C. to about 600° C.

3. The method of claim 1, wherein the solution comprises a solvent that is volatile at the temperature used to convert the gallium salt to the gallium oxide.

4. The method of claim 1, wherein the solution comprises an alcohol solvent.

5. The method of claim 1, wherein the amount of the gallium salt present in the solution is in the range from about 10% to about 50% by weight of the solution.

6. The method of claim 1, wherein the amount of the porogen present in the solution is in the range from about 3% to about 30% by weight of the solution.

7. The method of claim 1, wherein the porogen comprises a triblock copolymer of ethylene oxide and propylene oxide, a cetyltrimethylammonium chloride, $C_{16}H_{33}(OCH_2CH_2)_n OH$, or a combination comprising at least one of the foregoing compounds, wherein n is in the range from about 8 to about 12.

8. The method of claim 1, wherein the gallium salt comprises gallium nitrate hydrate, gallium chloride, gallium acetate, gallium sulfate, gallium citrate, or a combination comprising at least one of the foregoing compounds.

9. The method of claim 1, further comprising depositing an activating material into pores of the film.

10. The method of claim 1, further comprising depositing an activating material upon the film.

11. The method of claim 10, wherein the activating material comprises a hydrogen sensing material, gallium nitride, or a combination comprising at least one of the foregoing compounds.

12. The method of claim 1, further comprising exposing the film to an ammonia atmosphere to convert at least a portion of the gallium oxide to gallium nitride.

13. The method of claim 1, wherein the gallium oxide has a porosity of at least about 30%.

14. The method of claim 1, wherein the gallium oxide comprises a plurality of pores having a pore size in the range from about 2 nm to about 50 nm.

15. A method for patterning a gallium oxide film, the method comprising:
   providing a substrate upon which a gallium oxide film having a porosity of greater than about 30% resides;
   coating the substrate with a photoresist layer;
   exposing regions of the photoresist layer to actinic light;
   contacting the substrate with a photoresist developer comprising a hydroxyl compound to etch away select regions of the photoresist layer and underlying regions of the gallium oxide.

16. The method of claim 15, wherein said contacting comprises placing the substrate in a mixture comprising more than about 50 milliliters of the photoresist developer and deionized water.

17. The method of claim 15, further comprising aligning a mask plate to the gallium oxide film before exposing the regions of the photoresist layer not blocked by the mask plate to the actinic light.

18. The method of claim 15, further comprising removing the remaining regions of the photoresist layer from the gallium oxide film after etching the regions of the gallium oxide film.

19. The method of claim 15, wherein the select regions of the photoresist layer removed by the photoresist developer are the regions exposed to the actinic light.

20. The method of claim 15, wherein the select regions of the photoresist layer removed by the photoresist developer are regions not exposed to the actinic light.

21. The method of claim 15, wherein the gallium oxide film comprises a plurality of pores having a pore size in the range from about 2 nm to about 50 nm.

22. The method of claim 15, wherein the hydroxyl compound comprises potassium hydroxide, ammonium hydroxide, or a combination comprising at least one of the foregoing compounds.

* * * * *